(12) United States Patent
Marion

(10) Patent No.: US 8,410,322 B2
(45) Date of Patent: Apr. 2, 2013

(54) METHOD FOR PREPARING DINITROTOLUENE

(75) Inventor: Philippe Marion, Vernaison (FR)

(73) Assignee: Vencorex France, Saint-Priest (FR)

( * ) Notice: Subject to any disclaimer, the term of this patent is extended or adjusted under 35 U.S.C. 154(b) by 406 days.

(21) Appl. No.: 12/668,466

(22) PCT Filed: Jul. 8, 2008

(86) PCT No.: PCT/EP2008/058870
§ 371 (c)(1), (2), (4) Date: Feb. 24, 2010

(87) PCT Pub. No.: WO2009/010426
PCT Pub. Date: Jan. 22, 2009

(65) Prior Publication Data
US 2010/0145109 A1    Jun. 10, 2010

(30) Foreign Application Priority Data
Jul. 19, 2007    (FR) ...................................... 07 05231

(51) Int. Cl.
*C07C 205/00*    (2006.01)
(52) U.S. Cl. ...................................................... 568/934
(58) Field of Classification Search .................. 568/934
See application file for complete search history.

(56) References Cited

U.S. PATENT DOCUMENTS
7,495,136 B2 *    2/2009    Pohl et al. ..................... 568/934

FOREIGN PATENT DOCUMENTS
EP    0903336 A2    3/1999
WO    WO 2009/010426    1/2009

* cited by examiner

*Primary Examiner* — Jafar Parsa
(74) *Attorney, Agent, or Firm* — Michael B. Fein; Eckert Seamans Cherin & Mellott

(57) ABSTRACT

The present invention relates to a process for preparing dinitrotoluene. The process of the invention for preparing dinitrotoluene from mononitrotoluene, which comprises carrying out a mononitrotoluene nitration reaction using a nitrating mixture comprising nitric acid, sulphuric acid and water resulting in a two-phase medium and separating the organic and aqueous phases of said two-phase medium, is characterized in that the mononitrotoluene nitration is carried out using a nitrating mixture comprising at most 10% by weight of water resulting in a two-phase medium, in that the organic and aqueous phases of said two-phase medium are separated, and in that the aqueous phase derived from the separating operation is recycled, at the end of the mononitrotoluene nitration reaction and before the separation of the organic and aqueous phases, such that the weight ratio of the aqueous phase to the organic phase is at least equal to 1.2.

16 Claims, 1 Drawing Sheet

METHOD FOR PREPARING DINITROTOLUENE

CROSS-REFERENCE TO RELATED APPLICATIONS

Figure 1:
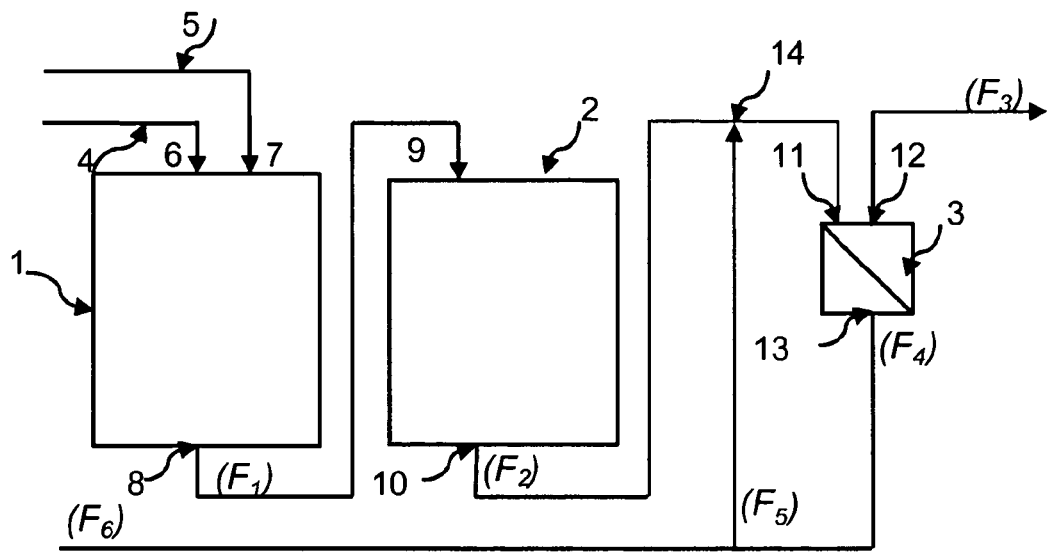

This application is a National Stage of International Application No. PCT/EP2008/058870 filed Jul. 8, 2008, which claims priority from French Application S.N. 07 05231 filed Jul. 19, 2007, which are hereby incorporated herein by reference in its entirety.

BACKGROUND OF THE INVENTION

The present invention relates to a method for preparing dinitrotoluene.

More precisely, the invention relates to an improved method for preparing dinitrotoluene from mononitrotoluene.

Dinitrotoluene is a significant industrial product since it is the production intermediate of toluene diisocyanate.

Dinitrotoluene is obtained by means of double nitration of toluene. Since the nitration operations are not selective, dinitrotoluene is an admixture of isomers of 2,4-dinitrotoluene and 2,6-dinitrotoluene associated with different impurities which are other isomers such as 2,3-dinitrotoluene, 2,5-dinitrotoluene, 3,4-dinitrotoluene and 3,5-dinitrotoluene. In the admixture, the ratio between the 2,4-dinitrotoluene and the 2,6-dinitrotoluene is equal to 4±0.3 and the content of impurities is generally between 3 and 4.5% by weight.

EP-A 0 903 336 describes a method for preparing dinitrotoluene by means of double nitration of toluene using an admixture of nitric acid and sulphuric acid with the characteristic of using dilute sulphuric acid.

Conventionally, the production of dinitrotoluene is carried out in accordance with a method in two steps as described in particular in the encyclopaedia KIRK-OTHMER, Encyclopedia of Chemical Technology, 15, p. 927 ff. ($3^{rd}$ edition) and by H. Hermann et al. in the work *Nitration, Recent Laboratory and Industrial Developments*, (Chapter 21, Lyle F. Albright, Richard V. C. Carr, Robert J. Schmitt, American Chemical Society, Washington D.C. 1996).

The first step involves carrying out the nitration of toluene with nitric acid, in the presence of sulphuric acid, and separating the mononitrotoluene obtained from the reaction admixture followed by a second step of nitration of the mononitrotoluene obtained using nitric acid and in the presence of sulphuric acid followed by separation of the dinitrotoluene obtained.

There is therefore carried out, in a first step, the nitration of the toluene using a nitrating admixture whose composition may vary and comprise, for example, from 50 to 60% by weight of sulphuric acid, from 15 to 40% by weight of nitric acid and from 10 to 20% by weight of water.

The quantity of nitric acid used is generally greater than the quantity required by the stoichiometry of the nitration reaction, the molar ratio of nitric acid/toluene being between 1.05 and 1.2.

After the reaction is complete, there is separation of an aqueous phase comprising the residual acids (sulphuric acid, nitric acid) with mainly sulphuric acid and an organic phase comprising mainly mononitrotoluene.

There is carried out in a following step the nitration of the mononitrotoluene included in the organic phase using a nitrating admixture.

Generally, it is advantageous, for reasons of productivity and equipment size, to begin with a nitrating admixture with a low water content. In this manner, an admixture is preferably used comprising from 55 to 70% by weight of sulphuric acid, from 20 to 44.5% of nitric acid and from 0.5 to 10% by weight of water.

The quantity of nitric acid used in this nitration reaction is greater than the quantity required by the stoichiometry of the reaction, the molar ratio of nitric acid/mononitrotoluene being between 1.05 and 1.2.

At the end of the reaction, there are obtained an aqueous phase and an organic phase which must be separated.

Under the conditions of a nitrating flow which is concentrated in terms of acids, the weight ratio, at the end of the dinitration reaction, between the aqueous phase and the organic phase is less than 1 and is more particularly between 0.75 and 0.95 which signifies that there is very preferably obtained an aqueous phase dispersed in the organic phase.

As mentioned above, it is important to use a nitrating admixture which is concentrated in terms of nitric and sulphuric acid.

Under these conditions, however, it has been found that separation of the organic and aqueous phases carried out in accordance with the technique of separation by decantation was laborious. In this manner, time periods of 48 hours were required in order to carry out the separation.

Furthermore, it has been shown that, since the technique of separation was found to be difficult, it was not possible to reduce the quantity of supernatant nitric acid used during the second nitration operation since, in this instance, the separation was made even more difficult even when the separation was carried out by means of centrifuging.

An object of the present invention is to provide an improved method for nitration of mononitrotoluene.

One of the objects of the invention is to provide a method which allows easier separation of the aqueous and organic phases following the operation for nitration of the mononitrotoluene.

Another object of the invention is to allow the quantity of supernatant nitric acid used in the second nitration step to be reduced and thus to reduce the quantity of nitric acid present in the dinitrotoluene subsequently sent for purification by means of washing: the supernatant nitric acid will then be found in the aqueous effluents of the method which may be recycled or processed.

SUMMARY OF THE INVENTION

According to the present invention, it has been found that it was possible to facilitate the separation of the aqueous and organic phases and to lower the quantity of supernatant nitric acid since there was carried out, prior to the separation of the phases, a phase inversion, that is to say that the organic phase was dispersed in the aqueous phase.

This continuous phase change functions by modifying the ratio between the aqueous phase and the organic phase and by selecting the weight ratio between the aqueous phase and the organic phase to be greater than 1.2, preferably between 1.5 and 3.5, and even more preferably between 1.8 and 3.0.

More precisely, the present invention relates to a method for preparing dinitrotoluene from mononitrotoluene which involves the nitration reaction of mononitrotoluene using a nitrating admixture which comprises nitric acid, sulphuric acid and water and which results in a bi-phase medium, then separation of the organic and aqueous phases of the bi-phase medium, which is characterised in that the nitration of the mononitrotoluene is carried out using a nitrating admixture which comprises a maximum of 10% by weight of water resulting in a bi-phase medium, in that the organic and aqueous phases of the bi-phase medium are separated, and in that the aqueous phase from the separation operation is recycled, at the end of the nitration reaction of the mononitrotoluene and before the separation of the organic and aqueous phases such that the weight ratio between the aqueous phase and the organic phase is at least 1.2.

In this manner, in accordance with the method of the invention, the ratio of the aqueous and organic phases is adjusted by recycling the aqueous phase which comprises mainly sulphuric acid and which is recovered following the separation of the organic and aqueous phases.

The introduction of an aqueous flow of sulphuric acid is carried out upstream of the operation for separating the aqueous and organic phases and allows a continuous phase change to be carried out and thus better separation of the aqueous and organic phases since the decantation time becomes less than 1 minute.

Furthermore, it becomes possible to reduce the excess of nitric acid used, without impairing the nitration operation of the invention. It is set out by way of example that the quantity of nitric acid can be reduced by from 50 to 75% by weight.

It should be noted that the introduction of the acid aqueous phase is carried out in the bi-phase medium which results from the nitration of the mononitrotoluene.

However, the introduction location may occur when the conversion level of the nitrotoluene is equal to or close to 100% but also when it is less but preferably at least 90%.

The term "end of nitration reaction" is intended to refer to a conversion level of nitrotoluene of at least 90%.

The term "conversion level" (TT) is intended to refer to the ratio between the number of moles of nitrotoluene converted and the number of moles of nitrotoluene used.

It is commonplace to carry out nitration operations in a series of reactors, in particular in a sequence of at least two reactors, the first reactor(s) referred to as "nitration reactors" allowing the nitration of the mononitrotoluene to be carried out with a conversion level of at least 90% associated with a second type of reactor referred to as a "finishing reactor" which allows the conversion level to be improved up to a level equal to or close to 100%.

The finishing reactor is distinguished from the previous ones by the fact that it does not involve the introduction of an admixture of nitrating acids.

In this manner, the invention includes the case in which the separated acid aqueous phase is added, at the end of the nitration reaction, downstream of the nitration reactor(s) and upstream of or in the region of the finishing reactor.

DETAILED DESCRIPTION

In accordance with the method of the invention, the starting point is a solution of nitrotoluene which can be prepared in conventional manner in accordance with the techniques described in literature.

According to a preferred embodiment, there is carried out in a first step the nitration of the toluene with the nitric acid, in the presence of sulphuric acid which results in a bi-phase medium which is then subjected to a separation operation in order to obtain, on the one hand, an aqueous phase and, on the other hand, an organic phase comprising mainly mononitrotoluene which will then be subjected to a subsequent nitration operation.

The first nitration operation can be carried out in a discontinuous manner (batch) but the continuous method is preferred.

According to a discontinuous method, the toluene is introduced into a cooled reactor (approximately 25° C.) then the nitration thereof is carried out using an admixture which generates nitronium ions $NO_2^+$ and whose composition may vary and comprise, for example, from 50 to 60% by weight of sulphuric acid, from 15 to 40% of nitric acid and from 10 to 20% by weight of water.

The nitration reaction must be carried out in a reactor which has good levels of effectiveness in terms of material transfer and heat transfer.

It is possible to use, for example, the Meissner loop reactor in which the agitation is carried out by means of a circulator or the Biazzi reactor which is an agitated vessel.

The quantity of nitric acid used is greater than the quantity required by the stoichiometry of the reaction. The molar ratio of nitric acid/toluene is between 1.05 and 1.2.

The admixture is added progressively into the toluene whilst the reaction admixture is kept at 25° C.

After the addition of the nitrating admixture, the temperature rises to between 35 and 55° C.

The mononitration reaction of the toluene is generally carried out under atmospheric pressure, although higher pressures can also be used.

According to a preferred variant of the method of the invention, this nitration step is carried out under a controlled atmosphere of inert gases so as to be under concentration conditions of gaseous products in the atmosphere outside the inflammability zone. It is possible to establish an atmosphere of rare gases, preferably argon, but it is more economical to use nitrogen.

After the reaction is complete, there is separation of an organic phase which comprises mainly mononitrotoluene and an aqueous phase which comprises the residual acids with mainly sulphuric acid.

The separation can be carried out in accordance with conventional liquid/liquid separation techniques such as centrifuging or static decantation.

According to a continuous embodiment, there is generally first charged the lower portion of a vessel which comprises an aqueous solution of sulphuric acid, that is to say, a solution which has a concentration of sulphuric acid which is, for example, between 65 and 80% by weight.

The toluene and the admixture of nitric acid and sulphuric acid are supplied in parallel so that the ratio of nitric acid/toluene is complied with and the titre of sulphuric acid is controlled, being discharged in the flow of residual acids.

At the end of the mononitration reaction, an organic phase is obtained which comprises mainly mononitrotoluene and more precisely:

from 75 to 97% by weight of mononitrotoluene,
from 2 to 15% by weight of dinitrotoluene,
from 1 to 10% by weight of nitric acid,
and less than 1% of water and sulphuric acid.

In accordance with the method of the invention, the nitration of the organic phase comprising the mononitrotoluene is carried out using nitric acid in combination with sulphuric acid. The invention does not exclude the use of oleums. It is therefore possible to use oleums which correspond to sulphuric acid charged with sulphuric anhydride $SO_3$ whose concentration may be between 10% and 40% by weight. Oleums having 20% and 40% by weight of $SO_3$ are commercially available.

It is preferable to use a nitrating admixture having a low water content and more specifically a nitrating admixture comprising from 55 to 70% by weight of sulphuric acid, from 20 to 44.5% of nitric acid and from 0.5 to 10% by weight of water.

Preferably, a water content of between 0.5% and 9% by weight is selected.

In the same manner as in mononitration, this step can be carried out in a discontinuous manner but preferably in accordance with a continuous embodiment.

In this manner, in a nitration reactor as described above, the organic phase and the nitrating admixture are introduced in parallel.

Two parameters are taken into account in order to determine the flow rate of the two flows, that is to say, the molar ratio of nitric acid/mononitrotoluene and the concentration of sulphuric acid recovered in the aqueous phase of the residual acids.

The flow rate of the two flows is determined so that the molar ratio of nitric acid/mononitrotoluene is between 1.03 and 1.25.

According to a preferred embodiment of the invention, the concentration of nitric acid in the medium can be lowered and the molar ratio of nitric acid/mononitrotoluene selected in the lower part of the range, that is to say, advantageously selected so as to be between 1.03 and 1.15.

The flow rate of the flows is also adapted so that the content of sulphuric acid present in the aqueous phase from the separation is between 70 and 90%, preferably between 74 and 83.5% by weight of sulphuric acid expressed relative to the weight of all the constituents including the organic compounds of the aqueous phase.

The method of the invention is advantageously carried out at a temperature of between 50 and 90° C., preferably between 60° C. and 80° C.

It should be noted that the dinitration reaction can be carried out in a reactor or in a series of reactors, for example, 2 or 3 reactors whose temperature may be equal or different: in this instance, generally the temperature selected in the above-mentioned range increases from the first reactor to the last.

The nitration reaction of the mononitrotoluene is generally carried out under atmospheric pressure, although higher pressures can also be used.

According to a preferred variant of the method of the invention, this nitration step is carried out under a controlled atmosphere of inert gases, in order to be under concentration conditions of the gaseous products in the atmosphere outside the inflammability zone. An atmosphere of nitrogen is preferably established.

At the end of the reaction, an aqueous phase and an organic phase are obtained which must be separated.

The separation of the aqueous and organic phases is an operation which can be carried out, for example, in a centrifuge or a static decanter.

Beforehand, however, in accordance with the method of the invention, there is carried out, after the operation for nitration of dinitrotoluene and before the separation of the organic and aqueous phases, the addition of the aqueous phase recovered following the separation of the organic and aqueous phases so that the weight ratio between the aqueous phase and the organic phase is at least equal to 1.2, preferably between 1.5 and 3.5, and more preferably between 1.8 and 3.0.

It is possible to recycle the aqueous phase recovered following the separation operation which can be carried out, for example, in a centrifuge or a static decanter.

It is preferable to recycle a fraction of the recovered aqueous phase, preferably less than 90% by weight and even more preferably, from 40 to 80% by weight, the other acid aqueous fraction being able to be recycled upstream of the method, in particular as a source of sulphuric acid at the step for mononitration of the toluene.

The recycling flow rate of the acid aqueous phase is calculated so that the weight ratio between the aqueous phase and the organic phase is at least equal to 1.2, preferably between 1.5 and 3.5, and even more preferably between 1.8 and 3.0.

The introduction of the acid aqueous flow upstream of the separation can be carried out, for example, using a device for mixing the main bi-phase flow and the acid aqueous flow, such as, for example, a static mixer.

In this manner, after recycling the acid aqueous phase before the separation operation, the preferred composition of the aqueous and organic phases is as follows:

the aqueous phase comprising mainly sulphuric acid has the following composition:
 from 74 to 83.5% by weight of sulphuric acid,
 from 0.5 to 3.5% by weight of nitric acid,
 from 8 to 18.5% by weight of water,
 from 4 to 8% by weight of soluble dinitrotoluene,
 the organic phase comprising mainly dinitrotoluene has the following composition:
 from 89.25% to 98.77% by weight of dinitrotoluene,
 from 1 to 7% by weight of nitric acid,
 from 0.1 to 2% by weight of sulphuric acid,
 from 0.03 to 1.5% by weight of water,
 from 0.1 to 0.25% by weight of organic impurities (dinitrocresols, trinitrocresols, dinitrobenzoic acid).

According to a preferred variant of the method of the invention, the aqueous phase comprises a lower concentration of nitric acid which is advantageously between 0.5 and 1.5%.

The method of the invention is particularly advantageous since it allows a reduction in the decantation separation times which may be from less than 1 minute to 30 seconds.

When changing from a continuous organic phase system to a continuous aqueous phase system, it is possible to reduce the excess of nitric acid used during the second nitration reaction.

An example is set out below of an installation in which the method of the invention can be used and which comprises:

a reactor for nitration of mononitrotoluene provided with means for introducing the reagents (mononitrotoluene, nitrating admixture), heating means, an agitation system and, in the lower portion thereof, a system for tapping the reaction admixture, a second reactor for finishing the nitration reaction, which is connected by means of a conduit to the outlet of the first reactor and which is provided with means for introducing the reaction admixture from the first reactor and, in the lower portion thereof, a system for tapping the reaction admixture, a device for separating the organic and aqueous phases (preferably a decanter, centrifuge) connected to the outlet of the second reactor by means of a conduit, a means for introducing a fraction of the acid aqueous phase from the separation operation of the organic and aqueous phases, either in the region of the conduit which connects the second finishing reactor to the phase separation device, or upstream of the second finishing reactor on the conduit which connects the outlet of the nitration reactor to the inlet of the second finishing reactor or directly to the inlet of the finishing reactor.

The various items of equipment are connected by means of pipes which circulate and recycle the reagents.

Figure 2:
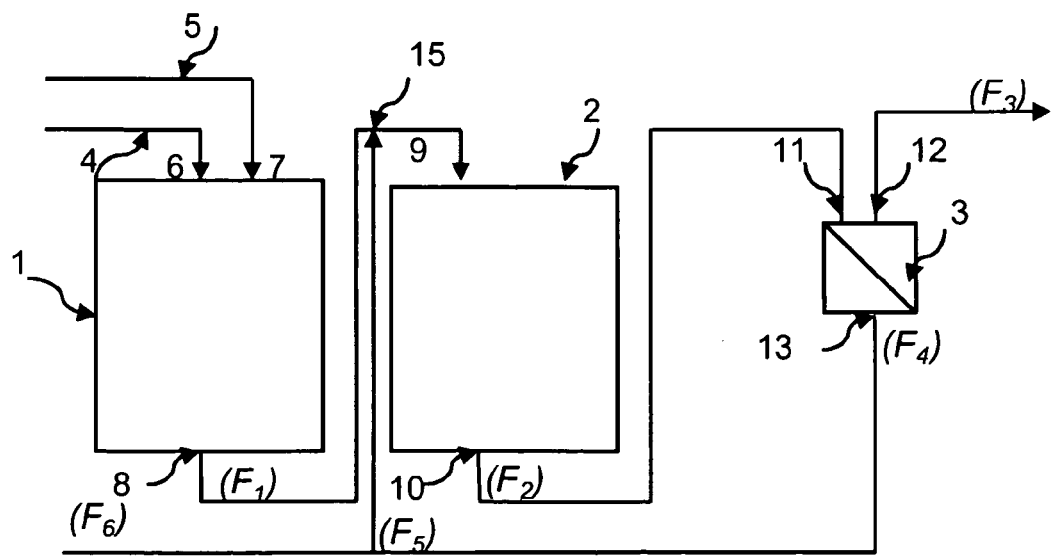

Two practical embodiments of the invention are illustrated in the appended drawings in the form of FIGS. 1 and 2.

FIGS. 1 and 2 are schematic illustrations of the various items of equipment which are suitable for the implementation of the invention and which differ from each other owing to the introduction location of the acid aqueous phase.

The assembly described in FIG. 1 comprises a reactor (1) for nitration of the mononitrotoluene, into which the mononitrotoluene (4) and the nitrating admixture (5) are introduced at (6) and (7), respectively.

The reaction admixture ($F_1$) being discharged from the reactor (1) at (8) is introduced at (9) into a second reactor (2) in which the nitration reaction is finished.

Upon discharge from the second reactor (2) at (10), a bi-phase liquid ($F_2$) is recovered which will be subjected to a separation operation which, in FIG. 1, is a decanter (3) which allows the separation at (13) of an acid aqueous phase ($F_4$) and at (12) an organic phase ($F_3$) of dinitrotoluene which can optionally be sent for purification.

The acid aqueous phase ($F_4$) is divided into two parts, a fraction ($F_5$) and a fraction ($F_6$).

The fraction ($F_5$) of the acid aqueous phase is introduced via an appropriate device, for example, a static mixer or a circulator, on the conduit which connects the reactor (2) and the decanter (3) at a supply location (14) between (10) and (11).

The other fraction ($F_6$) of the acid aqueous phase is recycled upstream of the method.

FIG. 2 illustrates the equipment of FIG. 1 with the exception of the flow ($F_5$) which is recycled not upstream of the decanter (3) but instead, for example, via a branch at a location (15) between (8) and (9), upstream of the second reactor (2) or in the region of the inlet of the reactor (2).

EXAMPLES

The invention will now be described in greater detail with reference to embodiments taken by way of non-limiting example.

In the examples, the abbreviations have the following meaning:
MNT: mononitrotoluene,
DNT: dinitrotoluene,
SN: sulphonitric admixture,
AS: sulphuric acid,
AN: nitric acid.

Comparative Example 1

A continuous nitration reactor is supplied with 772 kg/h of unprocessed MNT containing 6.1% by weight of DNT and 91% by weight of MNT ($H_2SO_4$: 0.6% by weight and $HNO_3$: 2.3% by weight).

There is also co-supplied, at a rate of 1067 kg/h, a sulphonitric admixture which is made from 96% sulphuric acid and 99% nitric acid by weight.

The composition of the SN is AS: 62.8% by weight, AN: 34% by weight and water in sufficient quantity to obtain 100%.

The volume of the reactor is 200 litres.

The reaction temperature is 65° C.

The heat of the reaction is dissipated via heat exchangers.

The excess of nitric acid relative to MNT is 18 molar %.

At the outlet of the reactor, the two phases are separated by means of centrifuging.

A sample is removed upstream of the centrifuge.

A decantation time of approximately 48 hours is determined.

Comparative Example 2

The above test is reproduced but with the excess of nitric acid being lowered to 8 molar % which corresponds to 1022 kg/h of a sulphonitric admixture having 65.5% by weight of AS.

It should be noted that the separation of the phases becomes impossible, even by means of centrifuging, the operation having to be stopped.

A sample taken has not completely decanted after several days.

Example 3

A continuous nitration reactor is supplied with 772 kg/h of unprocessed MNT containing 6.1% by weight of DNT and 91% by weight of MNT ($H_2SO_4$: 0.6% by weight and $HNO_3$: 2.3% by weight). There is also co-supplied, at a rate of 1067 kg/h, a sulphonitric admixture which is made from 96% sulphuric acid and 99% nitric acid by weight.

The composition of the SN is AS: 62.8% by weight, AN: 34% by weight and water in sufficient quantity to obtain 100%.

The excess of nitric acid relative to MNT is 18 molar %.

At the outlet, the two phases are separated by means of centrifuging.

One part of the acid phase (that is, 65% by weight) is recycled as in FIG. 1, at the outlet of the finishing reactor, by means of a suitable mixing device (static mixer) or agitated small capacity device of 50l in this instance.

A sample of the supply of the centrifuge is taken after one hour.

The decantation time is in the order of 30 seconds.

The non-recycled part of the residual acid returns to the mononitration.

Example 4

Example 3 is reproduced with the exception of the excess of nitric acid which is reduced to 6 molar % (as opposed to an excess of 18 molar % in example 3).

The excess is controlled by measuring the nitric acid in the residual acid which changes from 2 to less than 1% by weight.

The decantation time of the sample taken from the supply of the centrifuge remains approximately 30 seconds.

The method of the invention which is based on a continuous phase change (continuous organic phase→continuous acid phase) made possible by the implementation of the recycling of the acid phase, allows a change from a decantation time measured at the supply of the centrifuges of 48 hours with a high excess of nitric acid (18 molar %) to a decantation time of 30 seconds with a reduced excess of nitric acid (6 molar %).

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

The invention claimed is:

1. A method for preparing dinitrotoluene from mononitrotoluene with improved decantation time comprising nitrating mononitrotoluene using a nitrating admixture which comprises nitric acid, sulphuric acid and water and which results in a bi-phase medium such that the weight ratio between the aqueous phase and the organic phase is at least 1.2, separating the organic and aqueous phases of the bi-phase medium, wherein the nitration of the mononitrotoluene is carried out using a nitrating admixture which comprises 20 to 44.5% of nitric acid, 55 to 70% by weight of sulphuric acid, a maximum of 10% by weight of water resulting in a bi-phase medium, separating the organic and aqueous phases of the bi-phase medium; and wherein the separated aqueous phase is recycled to a point at the end of the nitration reaction of the mononitrotoluene and before the separation of the organic and aqueous phases.

2. The method of claim 1, wherein the nitrating admixture comprises from 0.5 to 10% by weight of water.

3. The method of claim 1, wherein the organic phase comprising the mononitrotoluene and the nitrating admixture are introduced in parallel.

4. The method of claim 3, wherein the flow rate of the two flows is determined so that the molar ratio of nitric acid/mononitrotoluene is between 1.03 and 1.25.

5. The method of claim 4, wherein the concentration of nitric acid is such that the molar ratio of nitric acid/mononitrotoluene is selected so as to be between 1.03 and 1.15.

6. The method of claim 1, wherein the flow rate of the flows is also adapted so that the content of sulphuric acid present in the aqueous phase from the separation is between 70 and 90% by weight of sulphuric acid expressed relative to the weight of all the constituents including the organic compounds of the aqueous phase.

7. The method of claim 1, wherein the temperature of the nitration reaction of the mononitrotoluene is between 50 and 90° C.

8. The method according to claim 1, wherein the nitration reaction of the mononitrotoluene is carried out under atmospheric pressure under a controlled atmosphere of inert gases.

9. The method of claim 1, wherein the separation of the aqueous and organic phases is an operation which is carried out in a centrifuge or a static decanter.

10. The method of claim 1, wherein the addition of the aqueous phase from the separation operation of the organic and aqueous phases is carried out so that the weight ratio between the aqueous phase and the organic phase is between 1.5 and 3.5.

11. The method of claim 1, wherein the recycling of the aqueous phase to a point at the end of the nitration reaction of the mononitrotoluene and before the separation of the organic and aqueous phases is carried out using a device for mixing the main bi-phase flow and the acid aqueous flow.

12. The method of claim 1, wherein the aqueous phase, has the following composition:
from 74 to 83.5% by weight of sulphuric acid,
from 0.5 to 3.5% by weight of nitric acid,
from 8 to 18.5% by weight of water,
from 4 to 8% by weight of soluble dinitrotoluene.

13. The method of claim 12, wherein the aqueous phase comprises a concentration of nitric acid which is between 0.5 and 1.5% by weight.

14. The method of claim 1, wherein the organic phase has the following composition:
from 89.25% to 98.77% by weight of dinitrotoluene,
from 1 to 7% by weight of nitric acid,
from 0.1 to 2% by weight of sulphuric acid,
from 0.03 to 1.5% by weight of water,
from 0.1 to 0.25% by weight of organic impurities (dinitrocresols, trinitrocresols, dinitrobenzoic acid).

15. The method of claim 1, wherein the dinitrotoluene is an admixture of isomers of 2,4-dinitrotoluene and 2,6-dinitrotoluene.

16. The method of claim 15, wherein the ratio between the 2,4-dinitrotoluene and the 2,6-dinitrotoluene is equal to 4±0.3 and the content of impurities is between 3 and 4.5% by weight.

* * * * *